United States Patent [19]

Braquet et al.

[11] Patent Number: 5,075,322
[45] Date of Patent: Dec. 24, 1991

[54] SELENOPHEN DERIVATIVES, A PREPARATION PROCESS OF THE SAME AND THERAPEUTICAL COMPOSITIONS CONTAINING THEM

[75] Inventors: Pierre Braquet, Garches; Colette Broquet, Boulogne, both of France

[73] Assignee: Societe de Conseils de Recherches et d'Applications Scientifiques (S.C.R.A.S.), France

[21] Appl. No.: 613,149

[22] Filed: Nov. 14, 1990

[30] Foreign Application Priority Data

Nov. 22, 1989 [GB] United Kingdom ............... 8926392

[51] Int. Cl.$^5$ ............... A61K 31/445; C07D 421/14
[52] U.S. Cl. ............................. 514/320; 546/196
[58] Field of Search ............... 514/320; 546/196

[56] References Cited

U.S. PATENT DOCUMENTS 3,749,786 7/1973 Bourquin et al. ............... 514/324
3,853,915 12/1974 Bourquin et al. ............... 546/187

*Primary Examiner*—C. Warren Ivy
*Assistant Examiner*—Celia Chang
*Attorney, Agent, or Firm*—Lucas & Just

[57] ABSTRACT

The invention relates to new selenophen derivatives of the formulae,

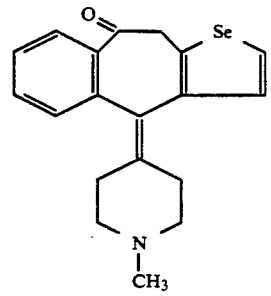

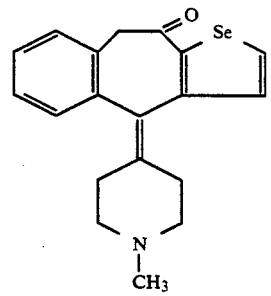

to a preparation process of said compounds and to therapeutic compositions containing the same.

2 Claims, No Drawings

SELENOPHEN DERIVATIVES, A PREPARATION PROCESS OF THE SAME AND THERAPEUTICAL COMPOSITIONS CONTAINING THEM

The present invention relates to new selenophen derivatives of the formulae:

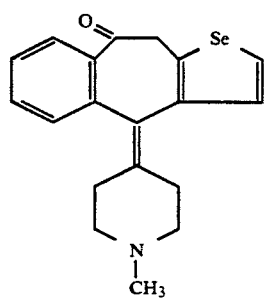

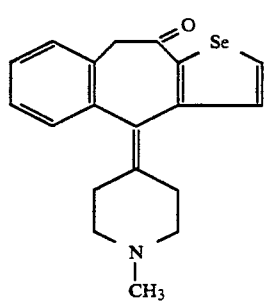

and to the therapeutically acceptable salts thereof.

The invention relates also to a preparation process of said compounds and to therapeutical compositions containing at least one of these compounds as an active ingredient therein.

These compounds and the starting material: 9,10-dihydro-4H-benzo [4,5] cyclohepta [1,2-b] selenophen 4-one (VI), may be prepared by the following succession of reactions:

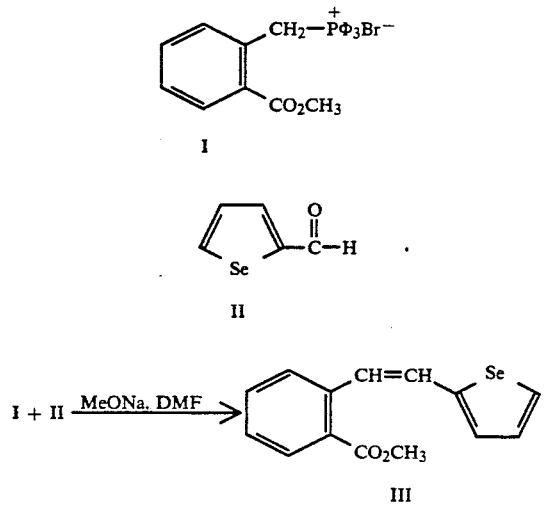

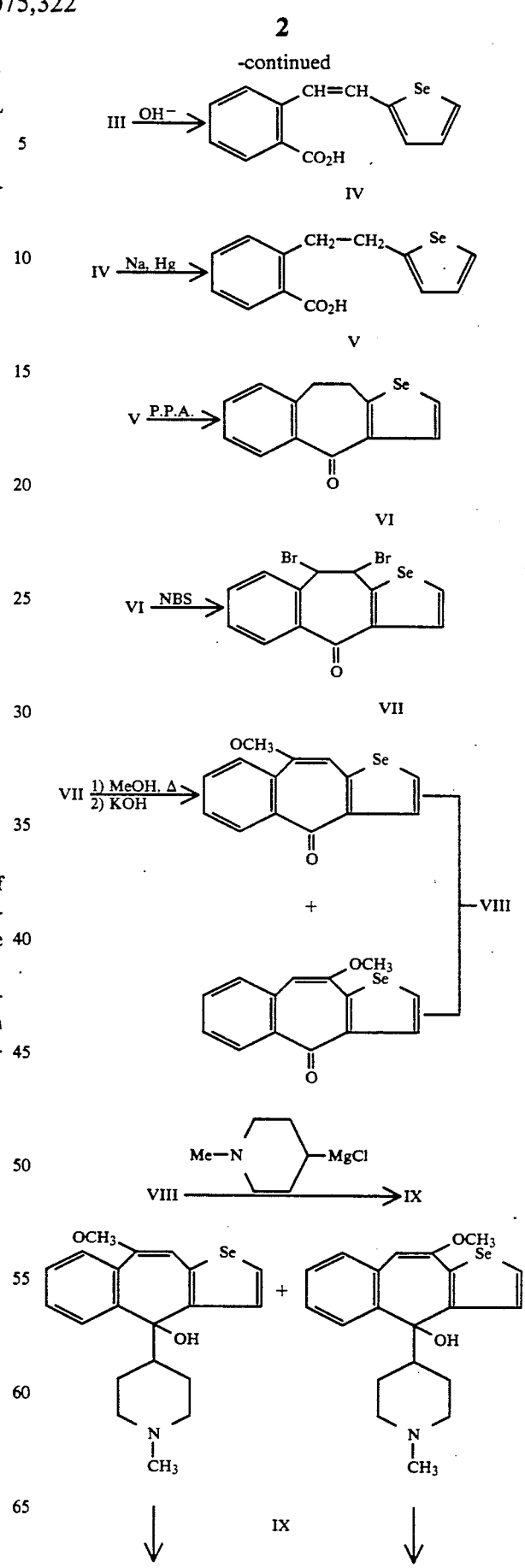

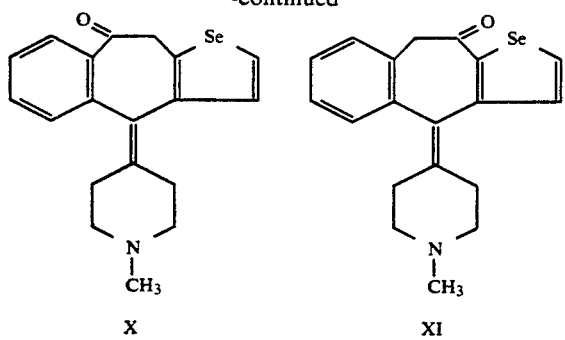

More precisely, the preparation process of the compounds of the invention, comprises brominating the 9,10-dihydro 4H benzo [4,5] cyclohepta [1,2-b] selenophen 4-one (VI), in an inert aprotic solvent under reflux, in presence of dibenzoylperoxide, by a large stoichiometric excess of N-bromo-succinimide, thereafter submitting the thus obtained 9,10-dibromo 4H benzo [4,5] cyclohepta [1,2-b] selenophen 4-one (VII), to reflux in methanol, then to the addition of a large stoichiometric excess of potassium oxide, at a temperature of from 60° C. to 90° C., then reacting slowly the mixture of 9-and 10-methoxy 4H benzo [4,5] cyclohepta [1,2-b] selenophen 4-one (VIII), at a temperature of from 20° to 25° C. in an aprotic solvent, with a large stoichiometric excess of [1-methylpiperidine 4-yl] magnesium chloride, and finally treating the obtained 4-hydroxy 4-[1-methyl 4-piperidyl] 9-and 10-methoxy benzo [4,5] cyclohepta [1,2-b] selenophen (IX), with hydrochloric acid, at a temperature of about 100° C., and separating by chromatography the compounds X and XI.

These compounds are more particularly interesting for their anti-allergic activity, which has been found to be more important than the one of the closely related compounds of the state of the art such as described in French patent 2.085.695.

This invention will be better understood from the description of the following examples. The successive examples correspond to the various steps appearing in the above reaction scheme.

EXAMPLE 1

(o-carboxybenzyl-triphenylphosphonium bromide)-methyl-ester I

This compound was obtained from triphenyl phosphine and (o-carboxybenzyl bromide)-methyl-ester.

EXAMPLE 2

2-formyl-selenophen II

This compound was prepared by the Vilsmeier-Haack reaction from selenophen, phosphorus oxychloride and DMF. $E_{10}=88°$ C. (yield 82%).

EXAMPLE 3

(Z+E)-2-[o-(methoxycarbonyl)styryl]selenophen III

To a suspension of o-carboxybenzyl triphenyl phosphonium bromide methyl ester I (39 g, 75 mmol) in 150 ml of dry DMF, at $-4°$ C., was added freshly prepared sodium methoxide (7 g; 0.13 mol). The red solution was stirred for 0.5 hour at the same temperature and 2-formyl selenophen (12 g, 75 mmol) in 35 ml DMF was added dropwise at $-4°$ C. The solution was stirred for 1.5 hours at room temperature. Ice and dilute HCl (15%) were added and the mixture was extracted with diethyl ether. Partial elimination of diethyl ether was followed by filtration of $\phi_3 PO$. The filtrate was evaporated and the residue was extracted several times with hexane. Elimination of hexane gave III as a viscous product, a Z+E mixture (17.5 g, yield 80%).

IR (cm$^{-1}$): 1720 (C=O); 1620 (C=C); 1600 ($\phi$); 1570 (selenophen)

$^1$HNMR (CDCl$_3$) (60 MHz) TMS. $\delta$: 7–8.1 (m, 9H); 3.95 (d, 3H, CH$_3$ Z/E=2.5. TLC rf: 0.76 (CHCl$_3$/MeOH, 95:5 V/V).

EXAMPLE 4

(Z+E)-2-(o-carboxystyryl)selenophen IV 10 g (36 mmol) of III were stirred with 150 ml of aqueous NaOH (0.5N) at 80–100° C. overnight.

Acidification and extraction with diethyl ether and evaporation gave IV as a Z+E mixture (6.8 g, yield 71%). mp 134° C.-TLC rf: 0.33 (CHCl$_3$/MeOH; 95:5; V/V).

IR (cm$^{-1}$): 3500–3000 (OH) (chelate); 1690 (C=O); 1620 (C=O); 1600 ($\phi$); 1570 (selenophen)

$^1$HNMR 60 MHz, CDCl$_3$. $\delta$: 11.65 (1H, OH); 7–8.1 (m, 9H).

EXAMPLE 5

2-(o-carboxyphenethyl)selenophen V

Sodium (4.7 g) was melted in dry toluene (20 ml) then mercury (225 g) was slowly added with stirring and the mixture was heated at 120° C. for 30 min. After elimination of toluene, the sodium amalgam was heated at 60° C. and a solution of IV (12 g) in ethanol 95 (130 ml) was added. Vigourous stirring was continued for 1 hour at the same temperature. Mercury was decanted, washed twice with ethanol. The solution was diluted with water (600 ml) then filtered through activated charcoal. The filtrate was acidified with concentrated HCl and the solid was filtered, washed with water and dried (8.5 g, yield 70%).

m.p. 118° C-TLC rf: 0.36 (CHCl$_3$/MeOH 95:5). IR (cm$^{-1}$): 3100–2900 (OH) (chelate); 1690 (C=O); 1600 ($\phi$); 1570 (selenophen).

$^1$HNMR 60 MHz CDCl$_3$ (TMS). $\delta$: 11.95 (1H, COOH); 7–8.2 (m, 7H); 3.3 (larg. sing., 4H, CH$_2$—CH$_2$).

EXAMPLE 6

9,10-dihydro 4H-benzo [4,5] cyclohepta [1,2-b] selenophen 4-one VI

A mixture of 30 g of polyphosphoric acid (PPA) and 30 ml of xylene was heated at 90° C. and V (8 g) was added.

The stirring was continued for 1 hour at 90° C., then the mixture was poured on ice. After extraction with toluene and washing with aqueous NaOH (30%) then with water, the organic phase was dried (Na$_2$SO$_4$) and evaporated. The brown residue was chromatographed on silica gel column (eluent petroleum ether/diethyl ether (PE/E) 95:5, then 90:10) and gave VI (5 g, yield 67%).

TLC rf: 0.42 (PE/E: 70:30),

IR (cm$^{-1}$): 1630 (C=O); 1600 (C=C ($\phi$)); 1530 (selenophen).

$^1$HNMR 60 MHz CDCl$_3$ (TMS). $\delta$: 7.2–8.1 (m, 6H); 3,2 (larg. sing., 4H, CH$_2$—CH$_2$).

EXAMPLE 7

9,10-dibromo 4H-benzo [4,5] cyclohepta [1,2-b] selenophen 4-one VII

A mixture of VI (4.6 g, 17.4 mmol), 57 ml of dry $CCl_4$, N-bromo succinimide (6.6 g, 36 mmol) and dibenzoylperoxide (0.3 g) was refluxed for 3 hours with stirring. Succinimide was filtered off and washed with CCl and the filtrate was eliminated.

The crude product obtained VII was worked up without purification.

IR ($cm^{-1}$): 1640 (C=O); 1595 ($\phi$); 1540 (selenophen)
$^1$HNMR 60 Mz $CDCl_3$ (TMS). $\delta$: 7–8 (m, 6H); 6.05 (q, 1H, CHBr); 5.6 (q, 1H,CHBr).

EXAMPLE 8

9-and 10-methoxy 4H-benzo [4,5] cyclohepta [1,2-b] selenophen 4-one VIII (as a mixture)

A solution of crude product VII in methanol (80 ml) was refluxed with stirring for 6 hrs. Then KOH (3.3 g) was added and the mixture was heated for 6 hrs. The solid was filtered off at room temperature and the filtrate was eliminated. The residue was chromatographed on silica gel column (eluent PE/E 98:2 then 95:5) and yielded 2.52 g of VIII (50% on the two steps).

m.p.: 191° C. (MeOH). TLC: 0.22 (PE/E 70:30) ratio 10/9=1.75. IR ($cm^{-1}$): 1580 (C=O); 1600 (C=C); 1540 (selenophen).

$^1$HNMR 60 MHz CDCl (TMS). $\delta$8.65 (d. 1H, $H_\alpha Se$); 8.25 (m, 1H, $H_\beta Se$); 7.6 (m, 4H, $\phi$); 6.5 (large sing, 1H, H—C=C—OMe); 4 (large sing., 3H, OMe).

EXAMPLE 9

4-hydroxy 4-[1-methyl 4-piperidyl] 9-and 10-methoxybenzo [4,5] cyclohepta [1,2-b] selenophen IX A solution of 4-chloro 1-methyl piperidine (4 g) in dry THF (10 ml) was added dropwise to magnesium turnings covered with THF. The reaction was initiated by a drop of bromine, then the mixture was heated at 70° C. for 2 hrs. After cooling, the mixture was diluted with 40 ml THF, then a solution of VIII (2.2 g) in 20 ml THF was added dropwise at room temperature and the mixture was stirred for 2 hrs, then poured in ice and $NH_4Cl$, and extracted with $CHCl_3$. The organic phase was washed with water, dried ($Na_2SO_4$) and evaporated. The residue was chromatographed on silica gel column (eluent $CHCl_3$, $CHCl_3$/MeOH 95:5 then 90:10) and gave IX (1.6 g, yield 54%).

TLC rf: 0.22 ($CHCl_3$/MeOH, 80:20). IR ($cm^{-1}$): 3400 (OH).

$^1$HNMR 60 $MH_3$ $CDCl_3$. $\delta$: 7–8.1 (6H); 6.2 (sing large, 1H, CH=C-OMe); 4.1 (1H, OH); 3.9 (2 peaks, 3H, $OCH_3$); 2.2 (sing, 3H, $NCH_3$); 1.8–2.7 (m, 9H)

EXAMPLE 10

4-(1-methyl 4-piperidyliden) 9,10-dihydro 4H-benzo [4,5] cyclohepta [1,2-b] selenophen 9-one X and 10-one XI 1.2 g of IX were dissolved in 10 ml HCl (3N) and heated for 1 hour at 100° C. with stirring.

After cooling, the solution was basified with NaOH and extracted with $CHCl_3$. The organic phase was dried and eliminated. A flash chromatography of the residue gave 2 products.

X eluted with $CHCl_3$/MeOH 99:1.

XI eluted with $CHCl_3$/MeOH 98:2.
TLC (eluent $CHCl_3$/MeOH 80:20):(rf X: 0.61; rf XI: 0.51).

IR ($cm^{-1}$): 1645 (C=O); 1580 ($\phi$); 1530 (selenophen).
$^1$HNMR. Product X: 60 MHz $CDCl_3$. $\delta$: 7.2 (m, 6H); 3.7 and 4.2 (2d, 2H, $CH_2$—C=O); 2.3 (sing., 3H, $NCH_3$); 2–2.8 (m, 8H, piperidine).

Product XI: 500 MHz $CDCl_3$.

$\delta$: 8.25 (d, 1H, $H_{60}Sc$); 7.25 (m, 5H); 4.25 and 3.8 (2 doublets, 2H, $CHH_2$—C=O); 2.3 (sing, 3H, $NCH_3$); 2.8 and 2.7 (2m, 2H, equatorial H in $\alpha$ of N); 2.6 and 2.4 (2m, 4H, H in $\alpha$ of C=C); 2.2 and 2.1 (2m, 2H, axial H in $\alpha$ of N)

SALTS

FUMARATES

Fumarate of XI

XI was dissolved in absolute ethanol and fumaric acid was added. The mixture was heated for few minutes and allowed to crystallize. After filtration, washing with ethanol and drying, pure fumarate was obtained, m.p.: 210°–212° C.

Fumarate of X

Proceeding similarly with XI, the pure corresponding fumarate was obtained, m.p.: 225° C.

TOXICITY

The toxicity of the compounds of the invention has been determined per os, by usual methods on mice. Their $LD_{50}$ values are from about 300 mg/kg.

PHARMACOLOGY

The compounds of the invention appear as anti-allergic agents. However, the compound XI has shown higher activity than compound X; this compound XI is an anti-allergic oral drug with histaminolytic and antianaphylactic properties. It prevents bronchial asthma. It is a powerful histamine and ovalbumine antagonist, and has been compared with ketotifen in pharmaceutical tests which are summarized as follow.

1°) Inhibition on ovalbumine immum bronchospasm

In the ovalbumine-induced bronchospasm in anaesthetized passively sensitized guinea-pigs, compound XI and ketotifen, administered 1 hour before the injection of ovalbumine, inhibit the bronchoconstriction (>90%) in a dose-dependant-manner respectively with following $ED_{50}$ (P.O.)

compound XI: $5.72.10^{-8}$M/kg. ketotifen: $9.41.10^{-8}$M/kg.

At 0.1 mg/kg and 0.05 mg/kg (P.O.), the kinetic study shows that the compound XI significantly inhibits the bronchoconstriction when administered 1 to 18 hours before ovalbumine injection. Ketotifen significantly inhibits the bronchoconstriction when administered 1 to 3 hours before ovalbumin injection; its activity then decreases from 6 to 15 hours. For both products, the activity disappears at 24 hours.

The kinetic results, after administration by oral route of the said compounds at 0.1 mg/kg and 0.05 mg/kg (P.O.), for 1 to several hours before ovalbumine injection (1 mg/kg), are reported respectively in tables 1 and 2.

The different symbols NS, *,  and * which may be found in the different tables, mean that the result is respectively not significative, significative, very significative and highly significant.

The same results are obtained in actively sensitized guinea pigs, after administration, by oral route, at 0.1 mg/kg (P.O.), 1 to 21 hours before ovalbumine injection (1 mg./kg); these results are reported in the following table 3.

In the case of passively sensitized rats, compound XI inhibits the bronchoconstriction in a dose-dependant manner whereas ketotifen has no effect in this model. The results are reported in following table 4.

2°) Inhibition on histamine immun bronchospasm

In the histamine (15 mg IV) induced bronchospasm in artificially ventilated anaesthetized guinea pigs, compound XI and ketotifen administered 1 hour before the injection of histamine, inhibit significantly the bronchoconstriction in a dose-dependant-manner, respectively with the following ED 50 (P.O.): compound XI 1.69 $10^{-8}$M/kg. ketotifen 6.35 $10^{-8}$M/kg.

But the kinetic study shows that compound XI totally inhibits the bronchospasm during the first 9 hours then shows a regularly decreasing inhibition and reaches a plateau between 15 and 24 hrs.

Ketotifen shows a maximum effect during only the first 3 hours.

The kinetic results of the administration of compound XI and ketotifen by oral route at 0.1 mg/kg (P.O.), 1 to 27 h histamine injection (15 mg IV), are reported in table 5.

3°) B.S.A.-induced immune lethality in mice

Compound XI shows a protective effect at 0.275 mg/kg (P.O.). At the same dose, ketotifen has no effect. The results of anaphylactic shock, in actively sensitized mice, are reported in table 6.

4°) Antagonistic activity against PAF effects

In vitro: effects on aggregation ($IC_{50}$) induced by PAF ($5 \cdot 10^{-10}$M), rat washed platelets are as follow: $IC_{50}$ Compound XI $2.10^{-6}$M. $IC_{50}$ Ketotifen $10^{-5}$M.

In vivo: in the PAF induced bronchospasm in artificially-ventilated anaesthetized guinea pigs, compound XI administrated 1 hour before the injection of PAF, significantly inhibits the bronchospasm at 0.1 mg/kg. Ketotifen is less active.

The dose-effect on PAF induced bronchoconstriction (60 mg/kg IV), are reported in table 7.

PRESENTATION-POSOLOGY

For oral administration, in human therapy, the compounds of the invention may be presented in gelatin capsules or phials, containing 0.05 to 0.1 mg of active ingredient per dose unit. Usual posology is from 0.05 to 0.4 mg per diem.

TABLE I

| Pretreatment period | Controls % of bronchoconstriction | Compound XI (0.1 mg/kg PO) % of bronchoconstriction | % of effect | ketotifen (0.1 mg/kg PO) % of bronchoconstriction | % of effect |
|---|---|---|---|---|---|
| 1 h | 84.5 ± 6.0 (n = 31) | 6.9 ± 1.0 (n = 13)*** | −91.5 ± 1.3 | 8.3 ± 3.2 (n = 12)*** | −90.2 ± 3.8 |
| 3 h | 62.3 ± 11.1 (n = 16) | 3.9 ± 1.1 (n = 5)*** | −93.7 ± 1.7 | 7.3 ± 3.0 (n = 5)*** | −88.3 ± 4.8 |
| 6 h | 62.3 ± 11.1 (n = 16) | 15.0 ± 11.5 (n = 6)* | −75.9 ± 18.4 | 31.9 ± 17.9 (n = 6) NS | −48.8 ± 28.8 |
| 9 h | 77.1 ± 12.2 (n = 6) | 35.7 ± 18.8 (n = 6)* | −60.1 ± 21.1 | 66.9 ± 19.7 (n = 6) NS | −25.1 ± 22.0 |
| 15 h | 78.8 ± 10.2 (n = 11) | 38.9 ± 13.7 (n = 10)* | −50.7 ± 17.3 | 77.5 ± 10.6 (n = 10) NS | −5.9 ± 13.3 |
| 18 h | 96.8 ± 1.7 (n = 10) | 36.8 ± 17.5 (n = 6)** | −62.0 ± 18.1 | 54.0 ± 18.6 (n = 6)* | −44.3 ± 19.2 |
| 21 h | 96.8 ± 1.7 (n = 10) | 73.3 ± 14.2 (n = 6)Lim* | −24.3 ± 14.7 | 88.3 ± 7.6 (n = 6) NS | −8.8 ± 7.9 |
| 24 h | 62.3 ± 11.1 (n = 16) | 45.4 ± 15.2 (n = 6) NS | −27.1 ± 24.4 | 67.3 ± 15.0 (n = 6) NS | +8.3 ± 24.0 |

TABLE II

| Pretreatment period | Controls % of bronchoconstriction | Compound XI (0.05 mg/kg PO) % of bronchoconstriction | % of effect | ketotifen (0.05 mg/kg PO) % of bronchoconstriction | % of effect |
|---|---|---|---|---|---|
| 1 h | 88.4 ± 6.9 (n = 17) | 13.2 ± 5.4 (n = 6)*** | −85.1% | 44.9 ± 15.9 (n = 6)** | −49.2% |
| 3 h | 89.6 ± 6.2 (n = 19) | 17.7 ± 7.0 (n = 7)*** | −80.5% | 5.7 ± 1.7 (n = 6)*** | −93.6% |
| 6 h | 96.7 ± 1.9 (n = 11) | 38.3 ± 16.5 (n = 7)*** | −60.4% | 82.9 ± 14.0 (n = 5) NS | −14.3% NS |
| 9 h | 96.8 ± 3.2 (n = 6) | 49.2 ± 16.7 (n = 6)* | −49.2% | 80.3 ± 19.7 (n = 5) NS | −17.1% |
| 15 h | 65.9 ± 19.0 (n = 6) | 61.6 ± 18.7 (n = 6) | −6.5% NS | 64.3 ± 18.3 (n = 6) | −2.4% NS |
| 18 h | 98.0 ± 1.4 (n = 9) | 50.7 ± 20.4 (n = 6)* | −48.3% | 100 ± 0 (n = 5) NS | +2.0% NS |
| 21 h | 98.0 ± 1.4 | 94.6 ± 4.4 | −3.5% | 94.4 ± 3.2 | −3.2% |

TABLE II-continued

| Pretreatment period | Controls % of broncho-constriction | Compound XI (0.05 mg/kg PO) % of broncho-constriction | % of effect | ketotifen (0.05 mg/kg PO) % of broncho-constriction | % of effect |
|---|---|---|---|---|---|
| | (n = 9) | (n = 5) | NS | (n = 5) | NS |

TABLE III

| Pretreatment period | Controls % of broncho-constriction | Compound XI (0.1 mg/kg PO) % of broncho-constriction | % of effect | ketotifen (0.1 mg/kg PO) % of broncho-constriction | % of effect |
|---|---|---|---|---|---|
| 1 h | 86.1 ± 10.5 (n = 8) | 3.5 ± 1.1 (n = 6)*** | −96.1 ± 1.3 | 3.6 ± 1.2 (n = 6)*** | −95.8 ± 1.4 |
| 3 h | 75.0 ± 11.7 (n = 12) | 5.0 ± 1.6 (n = 6)*** | −93.4 ± 2.1 | 3.3 ± 0.5 (n = 6)*** | −95.6 ± 0.7 |
| 6 h | 75.0 ± 11.7 (n = 12) | 2.1 ± 0.6 (n = 6)*** | −97.3 ± 0.8 | 42.1 ± 19.3 (n = 6) NS | −43.9 ± 25.8 |
| 9 h | 91.2 ± 8.8 (n = 5) | 35.5 ± 15.9 (n = 5)* | −61.1 ± 22.2 | 83.2 ± 16.1 (n = 6) NS | −8.8 ± 17.6 |
| 15 h | 85.2 ± 14.8 (n = 5) | 42.2 ± 16.6 (n = 6) | −50.6 ± 19.5 | 77.5 ± 14.8 (n = 6) NS | −9.0 ± 17.4 |
| 18 h | 54.7 ± 13.6 (n = 10) | 67.1 ± 19.0 (n = 6) NS | +22.7 ± 34.8 | 64.5 ± 19.5 (n = 6) NS | +17.9 ± 35.7 |
| 21 h | 54.7 ± 13.6 (n = 10) | 50.1 ± 21.6 (n = 5) NS | −8.3 ± 39.5 | 73.6 ± 15.5 (n = 6) NS | +34.4 ± 28.5 |

TABLE IV

| Compounds | Dose mg/kg PO | n | Percentage of bronchoconstriction | Percentage of effect |
|---|---|---|---|---|
| Controls | — | 15 | 38.5 ± 5.5 | — |
| Compound XI | 0.1 | 8 | 18.1 ± 6.3* | −49.4% |
| | 1 | 6 | 11.2 ± 2.7* | −68.7% |
| Ketotifen | 0.1 | 6 | 24.7 ± 5.1 NS | −31.0% |
| | 1 | 6 | 46.3 ± 11.0 NS | +29.3% |
| Astemizole | 5 | 5 | 8.6 ± 2.5** | −76.0% |

TABLE V

| Time | Controls % of broncho-constriction | Compound XI % of broncho-constriction | % of effect | ketotifen % of broncho-constriction | % of effect |
|---|---|---|---|---|---|
| 1 h | 79.4 ± 5.2 (n = 18) | 2.0 ± 0.8 (n = 8)*** | −97.5 ± 1.0 | 2.1 ± 0.8 (n = 9)*** | −97.4 ± 1.0 |
| 3 h | 79.4 ± 5.2 (n = 18) | 1.0 ± 1.0 (n = 3)*** | −98.8 ± 1.2 | 0 (n = 3)*** | −100 ± 0 |
| 6 h | 82.3 ± 8.1 (n = 5) | 5.4 ± 3.2 (n = 6)*** | −93.5 ± 3.8 | 18.2 ± 13.3 (n = 6)*** | −77.8 ± 16.2 |
| 9 h | 75.5 ± 10.6 (n = 6) | 4.9 ± 1.7 (n = 6)*** | −93.6 ± 2.3 | 22.1 ± 14.1 (n = 5)** | −71.5 ± 14.1 |
| 15 h | 70.7 ± 7.6 (n = 12) | 36.6 ± 8.4 (n = 10)* | −48.2 ± 11.8 | 51.4 ± 16.7 (n = 10) NS | −26.9 ± 16.7 |
| 18 h | 91.0 ± 3.4 (n = 7) | 34.9 ± 18.1 (n = 5)** | 61.7 ± 19.9 | 54.6 ± 13.3 (n = 5)* | −39.8 ± 14.8 |
| 21 h | 87.9 ± 4.5 (n = 6) | 52.9 ± 9.7 (n = 6)* | 37.6 ± 11.5 | 46.6 ± 14.9 (n = 6)** | −44.9 ± 17.6 |
| 24 h | 65.7 ± 7.8 (n = 11) | 37.9 ± 9.9 (n = 10)* | −42.3 ± 15.0 | 63.7 ± 15.1 (n = 6) NS | −3.0 ± 23.1 |
| 27 h | 72.3 ± 10.8 (n = 5) | 76.8 ± 10.2 (n = 5) NS | +6.3 ± 14.1 | 83.4 ± 5.9 (n = 6) NS | +15.4 ± 8.1 |

TABLE VI

| Compounds | Doses mg/kg PO | Number of killed | % of mortality | % of variation |
|---|---|---|---|---|
| Controls | — | 16/26 | 61.5 | — |
| Ketotifen | 0.250 | 5/10 | 50 | −18.7 NS |
| | 0.500 | 4/10 | 40 | −35 NS |
| Compound | 0.275 | 2/10 | 20 | −67.5** |
| XI | 0.550 | 1/10 | 10 | −83.7*** |
| Mequitazine | 2.5 | 3/10 | 30 | −51.2* |
| | 10 | 3/10 | 30 | −51.2* |

TABLE VII

| Compounds | Dose mg/kg PO | n | Percentage of bronchoconstriction | Percentage of effect |
|---|---|---|---|---|
| Controls | — | 18 | 78.3 ± 5.7 | — |
| Compound XI | 0.1 | 11 | 29.4 ± 7.9*** | −62.5 |
| | 1 | 6 | 23.0 ± 9.7*** | −70.6 |
| Ketotifen | 0.1 | 11 | 63.5 ± 9.6 NS | −18.9 |
| | 1 | 6 | 26.2 ± 14.8*** | −66.5 |

We claim:
1. Selenophen derivatives of the formulae:
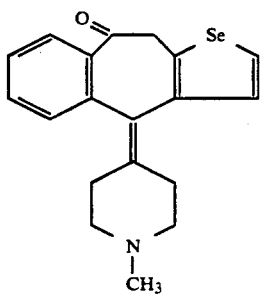
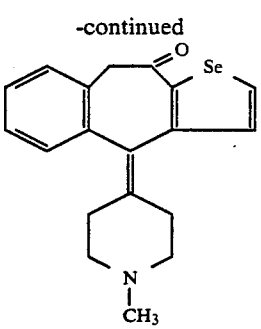
2. An antiallergic composition containing from 0.05 mg to 0.4 mg of at least one compound according to claim 1, associated with pharmaceutically acceptable diluents and/or carriers.